(12) United States Patent
Wada et al.

(10) Patent No.: US 7,714,125 B2
(45) Date of Patent: May 11, 2010

(54) PROCESS FOR PRODUCING PENAM COMPOUND USEFUL FOR PREPARING TAZOBACTAM

(75) Inventors: Isao Wada, Tokushima (JP); Yoshihisa Tokumaru, Tokushima (JP); Akihiro Shimabayashi, Tokushima (JP)

(73) Assignee: Otsuka Chemical Co., Ltd., Osaka (JP)

( * ) Notice: Subject to any disclaimer, the term of this patent is extended or adjusted under 35 U.S.C. 154(b) by 604 days.

(21) Appl. No.: 11/665,006

(22) PCT Filed: Oct. 25, 2005

(86) PCT No.: PCT/JP2005/019559

§ 371 (c)(1),
(2), (4) Date: Apr. 10, 2007

(87) PCT Pub. No.: WO2006/046539

PCT Pub. Date: May 4, 2006

(65) Prior Publication Data

US 2009/0012287 A1 Jan. 8, 2009

(30) Foreign Application Priority Data

Oct. 28, 2004 (JP) .............................. 2004-314409

(51) Int. Cl.
*C07D 499/04* (2006.01)
(52) U.S. Cl. .................................... 540/310
(58) Field of Classification Search .................. 540/310
See application file for complete search history.

(56) References Cited

U.S. PATENT DOCUMENTS

| 3,954,732 | A | | 5/1976 | Kamiya et al. |
| 4,056,521 | A | | 11/1977 | Kamiya et al. |
| 4,084,049 | A | | 4/1978 | Kamiya et al. |
| 4,164,497 | A | | 8/1979 | Kamiya et al. |
| 4,203,897 | A | | 5/1980 | Kamiya et al. |
| 4,218,374 | A | | 8/1980 | Kamiya et al. |
| 4,891,369 | A | | 1/1990 | Torii et al. |
| 4,933,444 | A | * | 6/1990 | Torii et al. .................. 540/313 |
| 6,936,711 | B2 | * | 8/2005 | Deshpande et al. ......... 540/310 |

FOREIGN PATENT DOCUMENTS

| JP | A-49-69694 | | 7/1974 |
| JP | A-63-264486 | | 11/1988 |
| JP | 7-121949 | | 12/1995 |
| KR | 344181 B | * | 7/2002 |

OTHER PUBLICATIONS

Deng Yong et al., *Synthetic Process of Tazobactam, β-Lactamase Inhibitor*, Zhongguo Yaowu Huaxue Zazhi *Chinese Journal of Medicinal Chemistry*, Apr. 2001; vol. 11, No. 2, pp. 93-95, Fig. 1, with English abstract on p. 95.

Deng Yong et al., *Synthetic Process of Tazobactam, β-lactamase Inhibitor*, Zhongguo Yaowu Huaxue Zazhi *Chinese Journal of Medicinal Chemistry*, Apr. 2001; vol. 11, No. 2, pp. 93-95, Fig. 1.

* cited by examiner

*Primary Examiner*—Mark L Berch
(74) *Attorney, Agent, or Firm*—Posz Law Group, PLC

(57) ABSTRACT

An object of the invention is to provide an industrially advantageous process capable of remarkably suppressing the generation of an undesirable by-product cepham compound to thereby efficiently produce a desired 2α-methyl-2β-[(1,2,3-triazol-1-yl)methyl]penam-3α-carboxylic acid ester. In the present invention, a diphenylmethyl 2β-bromomethyl-2α-methylpenam-3α-carboxylate (BMPB) is reacted with 1,2,3-triazole in a halogenated hydrocarbon solvent at −5° C. or lower. The reaction in a halogenated hydrocarbon solvent at −5° C. or less can remarkably suppress the generation of an undesirable by-product cepham compound, so that the desired diphenylmethyl 2α-methyl-2β-[(1,2,3-triazol-1-yl)methyl]penam-3α-carboxylate (TMPB) can be efficiently produced.

5 Claims, No Drawings

PROCESS FOR PRODUCING PENAM COMPOUND USEFUL FOR PREPARING TAZOBACTAM

TECHNICAL FIELD

The present invention relates to a novel process for producing a penam compound.

BACKGROUND ART

The 2α-methyl-2β-[(1,2,3-triazol-1-yl)methyl]penam-3α-carboxylic acid ester represented by formula (2)

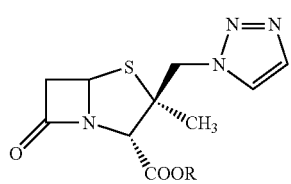

(2)

wherein R is a penicillin carboxyl protecting group, is a compound that is useful, for example, as an intermediate for producing a β-lactamase inhibitor.

The compound that is represented by formula (2) can be produced, for example, by reacting a 2'-halogenated penam compound represented by formula (1)

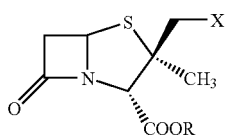

(1)

wherein X represents chlorine or bromine and R is as defined above, with 1,2,3-triazole (see Patent Document 1).

According to the Patent Document 1, a 2'-halogenated penam compound of formula (1) is reacted with 1,2,3-triazole in a solvent such as dimethylformamide, acetonitrile, acetone, tetrahydrofuran, dioxane, methanol, ethanol, etc., under temperature conditions in the range of 0° C. to 60° C.

However, when the 2'-halogenated penam compound of formula (1) is reacted with 1,2,3-triazole as described in Patent Document 1, a large amount of the by-product cepham compound represented by formula (3) is unavoidably generated as an isomer, with the result that the desired 2α-methyl-2β-[(1,2,3-triazol-1-yl)methyl]penam-3α-carboxylic acid ester represented by formula (2) cannot be obtained with a high yield.

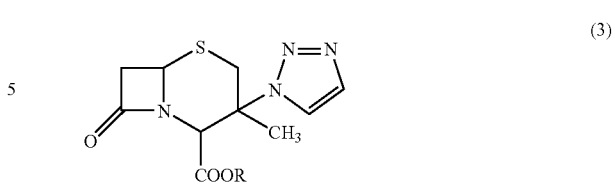

(3)

wherein R is as defined above.

Therefore, the development of an industrially advantageous process is desired that is capable of remarkably suppressing the generation of the by-product cepham compound of formula (3) to efficiently produce the 2α-methyl-2β-[(1,2,3-triazol-1-yl)methyl]penam-3α-carboxylic acid ester of formula (2). Patent Document 1: Japanese Examined Patent Publication No. 1995-121949

DISCLOSURE OF THE INVENTION

Problem to be Solved by the Invention

An object of the invention is to provide an industrially advantageous process that is capable of remarkably suppressing the generation of the by-product cepham compound represented by formula (3) to thereby efficiently produce the desired 2α-methyl-2β-[(1,2,3-triazol-1-yl)methyl]penam-3α-carboxylic acid ester represented by formula (2).

Means for Solving the Problem

The present inventors conducted extensive research in order to achieve the above object. As a result, the inventors found that when a 2'-halogenated penam compound represented by formula (1), wherein R is diphenylmethyl and X is bromine, is used as a starting material and the penam compound is reacted with 1,2,3-triazole in a specific reaction solvent under specific temperature conditions, the generation of the by-product cepham compound of formula (3), wherein R is diphenylmethyl, can be remarkably suppressed, so that the compound of formula (2), wherein R is diphenylmethyl, can be efficiently produced, thereby achieving the object of the invention. The present invention has been accomplished based on this finding.

The present invention provides the following production processes shown in items 1 to 5:

Item 1. A process for preparing a diphenylmethyl 2α-methyl-2β-[(1,2,3-triazol-1-yl)methyl]penam-3α-carboxylate comprising a step of reacting a diphenylmethyl 2β-bromomethyl-2α-methylpenam-3α-carboxylate with 1,2,3-triazole in a halogenated hydrocarbon solvent at −5° C. or lower.

Item 2. The process according to item 1 wherein the reaction is carried out in a mixed solvent of a halogenated hydrocarbon and a lower alcohol.

Item 3. The process according to item 1 wherein the reaction is carried out in the presence of a base.

Item 4. The process according to item 3 wherein the base is an anion exchange resin.

Item 5. The process according to item 1 wherein the reaction is carried out at −5° C. to −20° C.

The production process of the invention can be illustrated by the following reaction scheme:

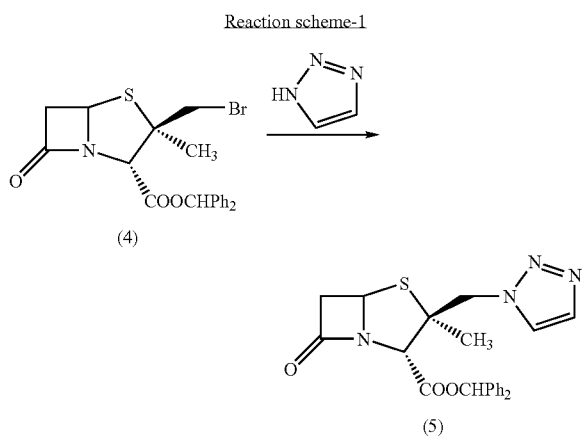

Reaction scheme-1

(4) → (5)

wherein Ph is phenyl.

As shown in Reaction scheme-1, the diphenylmethyl 2α-methyl-2β-[(1,2,3-triazol-1-yl)methyl]penam-3α-carboxylate represented by formula (5) (hereinafter sometimes referred to as "TMPB") can be produced by reacting a diphenylmethyl 2β-bromomethyl-2α-methylpenam-3α-carboxylate (hereinafter sometimes referred to as "BMPB") with 1,2,3-triazole.

A feature of the process of the invention is the use of BMPB represented by formula (4) as a starting material.

When the 2'-halogenated penam compound of formula (1), wherein R is diphenylmethyl and X is chlorine, is used as a starting material, it is impossible to achieve the object of the invention, even if the reaction is performed using the same reaction solvent under the same temperature conditions as those of the present invention. Similarly, even when a 2'-halogenated penam compound of formula (1), wherein R is diphenylmethyl and X is bromine, is used as a starting material, it is impossible to achieve the object of the invention, if the reaction is performed using a reaction solvent different from that of the present invention or under reaction conditions different from those of the present invention.

BMPB of formula (4) used as a starting material in the invention is a known compound, and can be easily produced according to known methods, such as the method disclosed in Japanese Unexamined Patent Publication No. 1983-4788, etc.

The reaction of the invention is performed in a halogenated hydrocarbon solvent.

Examples of halogenated hydrocarbons preferably used include dichloromethane, 1,2-dichloroethane, chloroform, etc. Dichloromethane and chloroform are particularly preferable. Such halogenated hydrocarbons can be used singly or in a combination of two or more.

The amount of halogenated hydrocarbon used is usually about 1 to about 50 liters, and preferably about 5 to about 10 liters, per kg of BMPB represented by formula (4).

When the reaction is carried out in a mixed solvent of a halogenated hydrocarbon and a lower alcohol according to the invention, the generation of the by-product cepham compound of formula (3), wherein R is diphenylmethyl, can be further suppressed.

Examples of lower alcohols include $C_{1-4}$ lower alcohols such as methanol, ethanol, isopropanol, etc. Such lower alcohols can be used singly or in a combination of two or more.

The proportion of lower alcohol to halogenated hydrocarbon may be about 0.01 to about 1 liter, and preferably about 0.1 to about 0.3 liters, of lower alcohol per liter of halogenated hydrocarbon.

The reaction of the invention is preferably performed in the presence of a base.

Examples of bases that can be used include alkali metal carbonates, such as sodium carbonate, potassium carbonate, etc.; alkali metal hydrogencarbonates, such as sodium hydrogencarbonate, potassium hydrogencarbonate, etc.; alkaline earth metal carbonates, such as calcium carbonate, etc.; anion exchange resins; etc. Such bases can be used singly or in a combination of two or more.

Among such bases, anion exchange resins are preferable. Weakly basic anion exchange resins are particularly preferable.

Examples of weakly basic anion exchange resins include styrene-divinylbenzene copolymers, styrene-acrylamide copolymers, etc. Specific examples include Amberlite IRA67, Amberlite IRA96SB, Amberlite XE583, and Amberlite XT6050RF manufactured by Organo Corp.; Diaion WA10, Diaion WA11, Diaion WA20, Diaion WA21 and Diaion WA30 manufactured by Mitsubishi Chemical, Corporation; etc.

Such a base is usually used in an amount of about 0.5 to about 5 equivalents, and preferably about 1 to about 2 equivalents, per equivalent of BMPB of formula (4). When an anion exchange resin is used, the amount is preferably about 0.5 to about 5 equivalents, and more preferably about 1 to about 2 equivalents, per equivalent of BMPB, expressed as a titer.

In the present invention, it is necessary to perform the reaction at −5° C. or lower. When the reaction is performed at temperatures higher than −5° C., the generation of an isomer represented by formula (3) cannot be sufficiently suppressed. Although it is advantageous to perform the reaction at temperatures lower than −20° C. in terms of suppressing the generation of the by-product isomer represented by formula (3), it takes a long time to complete the reaction. Therefore, the reaction is preferably carried out at a temperature in the range of −5° C. to −20° C. in the invention.

The reaction of the invention is usually completed in 5 hours or more, and preferably in about 10 to about 24 hours.

The desired compound obtained by the invention can be easily isolated from the reaction mixture by commonly used isolation techniques such as filtration, solvent extraction, re-crystallization, etc., and can be easily purified by commonly used purification techniques such as column chromatography, etc.

EFFECT OF THE INVENTION

The process of the invention can remarkably suppress the generation of the by-product cepham compound represented by formula (3), wherein R is diphenylmethyl, and thereby efficiently produce the compound of formula (2), wherein R is diphenylmethyl.

Therefore, the present invention can provide an industrially advantageous process for producing the compound represented by formula (2), wherein R is diphenylmethyl.

BEST MODE FOR CARRYING OUT THE INVENTION

Examples and Comparative Examples are given below to describe the invention in more detail. However, the invention is not limited to the Examples.

Example 1

180 ml of 1,2,3-triazole, 129.5 ml (titer: 1.06 meq/ml) of an anion exchange resin ("Diaion WA30, manufactured by Mitsubishi Chemical Corporation), and 118 ml of methanol were placed in a 1,000-ml reaction vessel. The resulting mixture was cooled to −7° C. and 400 ml of a dichloromethane solution containing 52.1 g of a diphenylmethyl 2β-bromomethyl-2α-methylpenam-3α-carboxylate (BMPB) was added at this temperature. The reaction was allowed to proceed while stirring at −5° C. for 17 hours. After completion of the reaction, the anion exchange resin was filtered off and washed with a small amount of dichloromethane. This wash and filtrate were washed with water four times to yield a dichloromethane solution containing a diphenylmethyl 2α-methyl-2β-[(1,2,3-triazol-1-yl)methyl]penam-3α-carboxylate (TMPB).

The proportions of TMPB and by-product diphenylmethyl 3-methyl-3-(1,2,3-triazol-1-yl)cepham-4-carboxylate (TCB) generated in the dichloromethane solution were determined by high-performance liquid chromatography (HPLC).

The proportions of TMPB and TCB in the dichloromethane solution were TMPB/TCB=6.34/1.

Example 2

A dichloromethane solution containing TMPB was prepared in the same manner as in Example 1 except that chloroform was used instead of dichloromethane.

The proportions of TMPB and by-product TCB generated in the dichloromethane solution were determined by HPLC.

The proportions of TMPB and TCB in the dichloromethane solution were TMPB/TCB=6.41/1.

Example 3

1.00 g of BMPB, 3.6 ml of 1,2,3-triazole, 2.6 ml of an anion exchange resin (Diaion WA30), and 8 ml of dichloromethane were placed in a 100-ml reaction vessel, and the resulting mixture was stirred at −5° C. for 17 hours. After completion of the reaction, the anion exchange resin was filtered off and washed with a small amount of dichloromethane. This wash and filtrate were washed with water four times to yield a dichloromethane solution containing TMPB.

The proportions of TMPB and by-product TCB generated in the dichloromethane solution were determined by HPLC.

The proportions of TMPB and TCB in the dichloromethane solution were TMPB/TCB=5.62/1.

Example 4

A dichloromethane solution containing TMPB was prepared in the same manner as in Example 1 except that the reaction was performed at −15° C. while stirring for 17 hours.

The proportions of TMPB and by-product TCB generated in the dichloromethane solution were determined by HPLC.

The proportions of TMPB and TCB in the dichloromethane solution were TMPB/TCB=7.01/1.

Comparative Example 1

A diphenylmethyl 2β-chloromethyl-2α-methylpenam-3α-carboxylate (CMPB) and 1,2,3-triazole were reacted in the same manner as in Example 4 of the Patent Document 1. More specifically, 1.00 g of CMPB, 3.6 ml of 1,2,3-triazole, 2.6 ml of an anion exchange resin ("Diaion WA30"), 5.3 ml of acetone, and 1.8 ml of water were placed in a 30-ml reaction vessel, and the resulting mixture was stirred at 40° C. for 3 hours. After completion of the reaction, the reaction mixture was cooled, and the anion exchange resin was filtered off and washed with a small amount of dichloromethane. This wash and filtrate were combined and extracted with 200 ml of dichloromethane.

The proportions of TMPB and by-product TCB generated in the extraction were determined by HPLC.

The proportions of TMPB and TCB in the dichloromethane extract were TMPB/TCB=4.55/1.

Comparative Example 2

43.5 g of CMPB, 200 ml of 1,2,3-triazole, 129.5 ml of an anion exchange resin ("Diaion WA30"), and 700 ml of dichloromethane were placed in a 2,000-ml reaction vessel, and the resulting mixture was stirred at 40° C. for 3 hours. After completion of the reaction, the reaction mixture was cooled, and the anion exchange resin was filtered off and washed with a small amount of dichloromethane.

The resulting wash and filtrate were combined, and the proportions of TMPB and by-product TCB in the mixture of wash and filtrate were determined by HPLC.

The proportions of TMPB and TCB in the dichloromethane solution were TMPB/TCB=4.20/1.

Comparative Example 3

The reaction was performed in the same manner as in Example 1 except that CMPB was used instead of BMPB. The reaction between CMPB and 1,2,3-triazole did not proceed, and TMPB was not generated.

The invention claimed is:

1. A process for preparing a diphenylmethyl 2α-methyl-2β-[(1,2,3-triazol-1-yl)methyl]penam-3α-carboxylate comprising a step of reacting a diphenylmethyl 2β-bromomethyl-2α-methylpenam-3α-carboxylate with 1,2,3-triazole in a halogenated hydrocarbon solvent at −5° C. or less.

2. The process according to claim 1 wherein the reaction is carried out in a mixed solvent of a halogenated hydrocarbon and a lower alcohol.

3. The process according to claim 1 wherein the reaction is carried out in the presence of a base.

4. The process according to claim 3 wherein the base is an anion exchange resin.

5. The process according to claim 1 wherein the reaction is carried out at −5° C. to −20° C.

* * * * *